United States Patent [19]
Corbett

[11] 3,971,385
[45] July 27, 1976

[54] MEDICAL TUBE WITH CUFF

[75] Inventor: Joseph H. Corbett, Glen Falls, N.Y.

[73] Assignee: Sherwood Medical Industries Inc., St. Louis, Mo.

[22] Filed: Sept. 9, 1974

[21] Appl. No.: 504,204

[52] U.S. Cl. .......................... 128/351; 128/349 B; 128/DIG. 21
[51] Int. Cl.² .......................................... A61M 25/00
[58] Field of Search .......................... 128/241–242, 128/245–246, 341–344, 347–351, DIG. 16, DIG. 21, 151–152; 3/36; 260/37.5 B

[56] References Cited
UNITED STATES PATENTS

| | | |
|---|---|---|
| 2,548,602 | 4/1951 | Greenburg .......................... 128/344 |
| 2,690,595 | 10/1954 | Raiche ............................. 128/349 B |
| 3,044,468 | 7/1962 | Birtwell ............................. 128/349 B |
| 3,638,655 | 2/1972 | Doherty ............................. 128/351 |
| 3,736,929 | 6/1973 | Mills ................................. 128/152 |
| 3,883,902 | 5/1975 | Lynch ............................. 128/462 X |
| 3,889,685 | 6/1975 | Miller, Jr. et al. ............... 128/349 B |

Primary Examiner—John D. Yasko
Attorney, Agent, or Firm—Stanley N. Garber; William R. O'Meara

[57] ABSTRACT

A medical tube, such as an endotracheal tube, having a balloon cuff filled with silicone gel.

13 Claims, 3 Drawing Figures

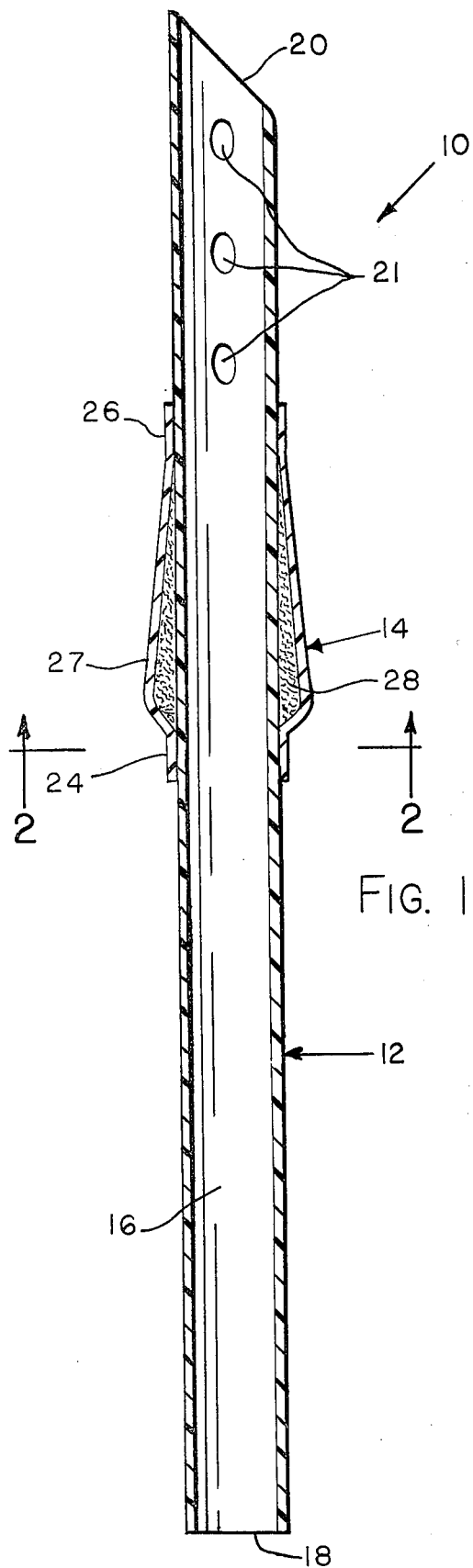
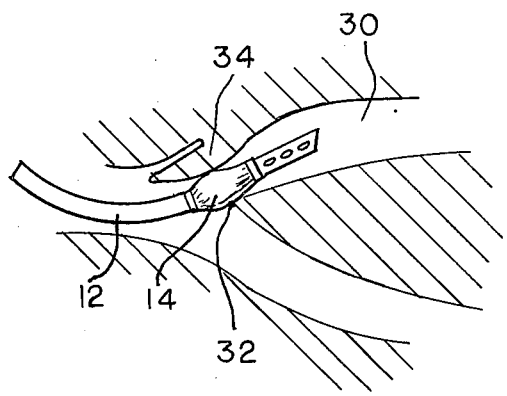
FIG. 3
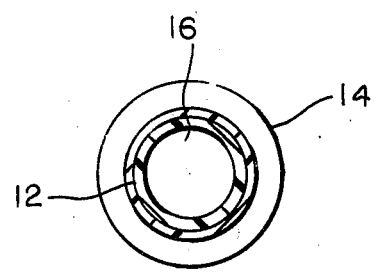
FIG. 2
FIG. 1

MEDICAL TUBE WITH CUFF

BACKGROUND OF THE INVENTION

This invention relates to medical tubes and more particularly to medical tubes having cuffs.

In many applications, medical tubes and catheters are provided with balloon cuffs for retention and/or providing a fluid seal between the tube and the body cavity or vessel in which the tube is inserted. For example, when a patient requires lung ventilation assistance or inhalation anesthesia, an endotracheal tube may be inserted through the larynx to the trachea and the balloon expanded or inflated to provide a seal between the tube and the walls of the trachea. Such tubes allow oxygen and other gases to be administered to the patient in controlled amounts with the tube remaining in the desired location and with the trachea sealed off from mucous and vomitus by the cuff.

In some cases, however, the use of medical tubes having inflatable balloon cuffs results in injury to the walls of the body cavity due to forces exerted by the cuff. Since the body cavity walls are generally irregular, considerable expansion or inflation pressure is often necessary to effect a good seal between the cuff and walls, and this tends to cause injury to the walls, especially where the tube remains in the same position for an extended period of time.

Various constructions, materials, and expansion or inflation mediums are used or have been proposed in attempts to avoid potential injury to the patient. In some cases, the balloon cuff is inflated by fluids, such as air, or by liquids, such as a saline solution or silicone oil. Sponge rubber has also been proposed for use in filling a cuff. However, such constructions and materials have not been entirely satisfactory. For example, excessive gas or liquid inflation pressures may be inadvertently used by the person inflating the cuff. The cuff or the filling medium may not be sufficiently soft or capable of readily conforming to small variations in the walls of a cavity so that relatively high pressures are needed. Also, where the medium in the cuff is air or liquid, it will readily flow out of the cuff with the cuff collapsing and no longer serving as a seal where even a small break or split occurs in the cuff.

SUMMARY OF THE INVENTION

Accordingly, it is an object of the present invention to provide an improved medical tube for specialized procedures having a cuff which substantially overcomes the above-mentioned undesirable features of the prior art.

Another object of the present invention is to provide a medical tube having a cuff which will provide a seal between the walls of the body cavity in which it is disposed and the tube while reducing the chance of injury to the cavity walls.

In accordance with the present invention, a medical tube is provided with a cuff containing a relatively soft gel.

These, as well as other objects and advantages of the present invention, will become apparent from the following detailed description and accompanying drawing wherein like reference numerals refer to like parts.

BRIEF DESCRIPTION OF THE DRAWING

FIG. 1 is an elevational sectional view of a medical tube in accordance with a preferred embodiment of the invention;

FIG. 2 is a sectional view taken along the line 2—2 of FIG. 1; and

FIG. 3 illustrates the medical tube of FIG. 1 inserted in a patient.

DESCRIPTION OF THE PREFERRED EMBODIMENT

Referring now to the drawing and particularly to FIGS. 1 and 2, a medical tube 10 is shown as an endotracheal tube which includes an elongated plastic tube or catheter 12 having a tapered balloon cuff 14 near the distal end of the tube.

Plastic tube 12 is preferably made of polyvinyl chloride, however, it may be of rubber or other suitable plastic material, such as polyethylene, polyurethane or the like, depending on the intended use of the tube. In the case of a tracheostomy tube, the tube 12 may be made of metal. Tube 12 has a lumen 16 extending through the tube from the proximal end 18 to the distal end 20. The distal tip is beveled for ease of insertion through the larynx and into the trachea of a patient. A plurality of holes 21 are shown extending through the wall of the tube 12 adjacent the distal end to insure that the tube provides a sufficient rate of fluid flow even if the distal end of lumen 16 is closed or partially closed by engagement with a wall of the body cavity.

Cuff 14 surrounds tube 12 and has a cylindrical proximal end portion 24 and a cylindrical distal end portion 26 which are sealingly connected, such as by a suitable adhesive, to the outer periphery of the tube. Cuff 14 has a balloon portion 27 which extends radially outwardly from the proximal end portion 24 and then tapers radially inwardly toward the distal end portion 26 to provide a generally conical configuration. The cuff 14 is formed of a relatively soft and pliable material, preferably a urethane film, although it may be formed of different materials such as a latex, silicone rubber, polyvinyl chloride or other plastic materials, depending on the desired characteristics and intended purpose of the tube. Cuff 14 may be preformed by a conventional dipping process in which a mold is dipped into a solution of the plastic or rubber material from which it is to be made, for example, liquid urethane, to form a film on the mold, curing the film, removing the film from the mold, and then securing it on the tube 12.

In accordance with the present invention, cuff 14 is filled with a relatively soft gel 28, preferably a medical grade silicone gel such as that conventionally used in prosthetics. For example, any well-known prosthetic gel, such as a silicone gel used in female breast prosthetics may be used. Preferably, the gel should have the consistency or "feel" of fatty tissue. Cuff 14 may be filled by mixing an uncured gel solution with a gelation or curing agent or catalyst and injecting the combined material into the cuff 14 by piercing the cuff by means of a hypodermic needle, and then allowing the material to cure or gel. A closure, such as a urethane patch (not shown) is adhesively secured to the cuff over the needle hole. In the illustrated embodiment, the interior wall of the cuff 14 and the exterior wall of tube 12 between the cuff end portions 24 and 26 define a liquid tight chamber to completely enclose and seal the gel 28 in the cuff.

Preferably, the gel material 28, after gelation, is homogeneous, that is, nonporous, noncellular, and nonabsorbable, for example, as opposed to a sponge rubber which has air cells and absorbs and holds liquid. The range of rigidity of gel 28, after gelation, is preferably substantially within a range of penetration values from about 4 mm. to about 120 mm. employing a conventional penetration test in which an aluminum plunger with a 1 ¾ inch diameter "Lexan" or plastic foot bears on the gel, the plunger and gel being heated to 125°C, and the total load on the gel being 19.5 grams. For example, one suitable gel for use in cuff 14 is a silicone prosthesis gel identified as "CRTV-6193" sold by General Electric Company. This gel is a two-part silicone liquid system that, after curing, forms a gel which is soft and pliable, and has a consistency of fatty tissue. The gel is an addition-cured, lightly-cured polydimethyl siloxane. In making the gel, a silicone-olefin polymer (liquid) is cross-linked to a silicone-hydride polymer (liquid) by means of an organo-metallic curing or gelling agent. The two liquids are preferably mixed, air bubbles removed, and then the mixture is introduced into the cuff by a hypodermic needle. The needle hole is patched and the gel cured for at least 2 hours at 95°C. Using the above-mentioned penetration test, this gel produced a penetration value of 5 mm. and the gel was transparent.

In FIG. 3, the medical tube 10 is shown disposed in a patient with the distal end portion in the trachea 30, and the cuff 14 wedged into the opening 32 of the trachea at the larynx 34. The cuff 14 serves as a tapered plug to provide a seal between the larynx walls at opening 32 and the exterior of tube 12 to seal the trachea and thereby permit positive ventilation of the lungs of the patient when the proximal end of the tube is connected to a source of oxygen (not shown). Controlled inhalation anesthesia may also, of course, be given through the tube 10. No fluid connection to the interior of the cuff or source of inflating or deflating fluid is, of course, used.

The silicone gel-filled cuff 14 is soft, supple and pliable, and readily conforms to the walls of the body cavity. When the endotracheal tube 10 is inserted into the trachea, it dilates the larynx but the cuff does not cause damage to the walls. The endotracheal tube 10 may be made in several different sizes, however, one given size is suitable for a range of tracheal opening sizes. Generally, a pediatric and two differently sized adult tubes are sufficient for most cases. Should a split occur in the wall of the cuff, the silicone gel, since it is coherent and does not flow like a liquid, will generally remain in the cuff. Where desired, the silicone gel may be x-ray opaque, for example, by adding barium sulfate to the pre-cured gel material.

In addition to the resiliency of the cuff 14, the gel 28 has a "memory" or tendency to return to an original conformation after deformation, which is unlike a liquid, so as to provide a good seal even though the walls of the body cavity are irregular. The preferred gel is homogeneous, that is, it is nonporous or has an uninterrupted or nonporous outer surface, so that it tends to conform to the cavity walls even though the wall surface has small irregularities; and this is accomplished without exerting excessively high pressures on the wall, as might otherwise occur where the material in the cuff is of a different material such as sponge rubber.

While an endotracheal tube has been described and illustrated, the present invention is applicable to many other types of medical tubes, such as different types of catheters, cannulas, and other tubes where a highly conformable cuff of predetermined size is used. For example, a nasal tube may be advantageously provided with a gel-filled cuff, with the cuff being used to close a nostral.

It is now apparent that there has been provided a novel medical tube having a cuff which meets the objects and advantages previously mentioned herein. It is understood that various changes and modifications to the embodiment illustrated and described herein may be made without departing from the true spirit and scope of the invention as defined in the claims which follow.

What is claimed is:

1. A medical tube insertable into a body cavity comprising an elongated tube for effecting fluid communication with the body cavity, a preformed cuff of smooth, pliable material connected to said tube in surrounding relation therewith and including proximal and distal portions sealingly connected to said elongated tube and a balloon portion between said proximal and distal portions spaced radially from said elongated tube, said balloon portion being axially spaced from the distal and proximal ends of said elongated tube and tapering radially outwardly from the distal end thereof toward the proximal end thereof, and a substantially nonporous, homogenous gel filling said balloon portion and conforming to the shape of said cuff, said cuff being conformable to the walls of the cavity it engages to provide a seal between the cavity walls and said elongated tube when disposed in said cavity.

2. The medical tube of claim 1 wherein the balloon portion has its maximum radial dimension substantially closer to its proximal end than to its distal end.

3. The medical tube of claim 1 for use as a tracheal tube wherein the outer surface of said cuff is conformable into sealing engagement with the walls of a trachea to form a seal between said tube and walls of the trachea when inserted therein.

4. The medical tube of claim 1 wherein said gel is a silicone gel.

5. The medical tube of claim 1 wherein said pliable material is a urethane film.

6. The medical tube of claim 1 wherein the rigidity of said gel is within the range of penetration values from 4 mm. to 120 mm. based on a penetration test which includes heating said gel to 125°C for two hours while allowing a plunger with a 1 ¾ inch diameter foot to bear on the gel, the total load that bears on the gel being 19.5 grams.

7. A medical endotracheal tube insertable into the trachea of a body comprising an elongated plastic tube for effecting fluid communication with the body trachea, a preformed cuff of smooth, pliable material connected to said tube in surrounding relation therewith and including proximal and distal portions sealingly connected to said plastic tube and a balloon portion between said proximal and distal portions spaced radially from said plastic tube, said balloon portion being spaced from the distal and proximal ends of said tube and tapering radially outwardly from the distal end thereof toward the proximal end thereof, and a substantially nonporous, homogenous gel filling said balloon portion and conforming to the shape of said cuff, said cuff being conformable to the walls of the trachea it engages to provide a seal between the trachea walls and said plastic tube when in use.

8. The medical endotracheal tube of claim 7 wherein said balloon portion has its maximum radial dimension substantially closer to its proximal end than to its distal end.

9. The medical endotracheal tube of claim 7 wherein said gel comprises a silicone gel.

10. The endotracheal tube of claim 7 wherein said plastic tube is polyvinyl chloride, and said cuff is a urethane film.

11. A medical tube insertable into a body cavity comprising an elongated tube for effecting fluid communication with the body cavity, a preformed cuff of smooth, pliable material connected to said tube in surrounding relation therewith and including proximal and distal portions sealingly connected to said elongated tube and a balloon portion between said proximal and distal portions spaced radially from said elongated tube, said balloon portion being axially spaced from the distal and proximal ends of said elongated tube and tapering radially outwardly from the distal end thereof toward the proximal end thereof so that it can be wedged into the body cavity, and a substantially nonporous, homogeneous, cured in situ, gel filling said balloon portion and conforming to the shape of said cuff, said cuff being conformable to the walls of the body cavity it engages when wedged therein to provide a seal between the body cavity walls and said elongated tube.

12. The medical tube of claim 11 wherein said gel comprises a silicone gel.

13. The medical tube of claim 12 wherein said cuff is formed of a material comprising urethane.

* * * * *